(12) United States Patent  (10) Patent No.: US 7,837,685 B2
Weinberg et al.  (45) Date of Patent: Nov. 23, 2010

(54) SWITCH MECHANISMS FOR SAFE ACTIVATION OF ENERGY ON AN ELECTROSURGICAL INSTRUMENT

(75) Inventors: Craig Weinberg, Denver, CO (US); Robert Sharp, Boulder, CO (US); Gary M. Couture, Longmont, CO (US); Darren Odom, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 138 days.

(21) Appl. No.: 11/180,949

(22) Filed: Jul. 13, 2005

(65) Prior Publication Data

US 2007/0016187 A1    Jan. 18, 2007

(51) Int. Cl.
   *A61B 18/14* (2006.01)
(52) U.S. Cl. .................. 606/42; 606/41; 606/51; 606/32; 606/1
(58) Field of Classification Search .............. 606/42, 606/37; 361/2–3, 1; 218/6, 7, 146, 154
   See application file for complete search history.

(56) References Cited

U.S. PATENT DOCUMENTS

| 371,664 | A |   | 10/1887 | Brannan et al. |
|---|---|---|---|---|
| 702,472 | A |   | 6/1902 | Pignolet |
| 728,883 | A |   | 5/1903 | Downes |
| 1,586,645 | A |   | 6/1926 | Bierman |
| 1,813,902 | A | * | 7/1931 | Bovie ................. 606/42 |
| 2,002,594 | A |   | 5/1935 | Wappler et al. |
| 2,011,169 | A |   | 8/1935 | Wappler |
| 2,031,682 | A |   | 2/1936 | Wappler et al. |
| 2,176,479 | A |   | 10/1939 | Willis |
| 2,305,156 | A |   | 4/1941 | Grubel |
| 2,279,753 | A | * | 4/1942 | Knopp ................. 200/4 |
| 2,632,661 | A |   | 8/1948 | Cristofv |
| 2,668,538 | A |   | 2/1954 | Baker |
| 2,796,065 | A |   | 6/1957 | Kapp |
| 3,372,288 | A | * | 3/1968 | Wigington ................. 327/402 |
| 3,459,187 | A |   | 8/1969 | Pallotta |
| 3,643,663 | A |   | 2/1972 | Sutter |

(Continued)

FOREIGN PATENT DOCUMENTS

CA          2104423         2/1994

(Continued)

OTHER PUBLICATIONS

Levy et al. " Use of a New Energy-based Vessel Ligation Device During Vaginal Hysterectomy" Int'l Federation of Gynecology and Obstetrics (FIGO) World Congress 1999.*

(Continued)

*Primary Examiner*—Thomas J. Sweet
*Assistant Examiner*—Ronald Hupczey, Jr.

(57) ABSTRACT

Various safe switching mechanisms are provided for use with electrosurgical instruments which prevent arcing between the high-energy contacts as the high-energy source is activated. The switching mechanisms generally include a pair of high-energy contacts and a pair of activation contacts. An actuator is provided which initially engages the high-energy contacts in advance of engagement of the activation contacts to prevent arcing and subsequently disengages the activation contacts in advance of the high-energy contacts as the energy source is deactivated. A method of switching power to an electrosurgical instrument while avoiding damage to high-energy contacts is also disclosed.

20 Claims, 4 Drawing Sheets

U.S. PATENT DOCUMENTS

| | | | |
|---|---|---|---|
| 3,651,811 A | 3/1972 | Hildebrandt et al. | |
| 3,720,896 A * | 3/1973 | Beierlein | 335/206 |
| 3,862,630 A | 1/1975 | Balamuth | |
| 3,863,339 A | 2/1975 | Reaney et al. | |
| 3,866,610 A | 2/1975 | Kletschka | |
| 3,911,766 A | 10/1975 | Fridolph et al. | |
| 3,920,021 A | 11/1975 | Hiltebrandt | |
| 3,921,641 A | 11/1975 | Hulka | |
| 3,938,527 A | 2/1976 | Rioux et al. | |
| 3,952,749 A | 4/1976 | Fridolph et al. | |
| 3,970,088 A | 7/1976 | Morrison | |
| 3,987,795 A | 10/1976 | Morrison | |
| 4,005,714 A | 2/1977 | Hiltebrandt | |
| 4,041,952 A | 8/1977 | Morrison, Jr. et al. | |
| 4,043,342 A | 8/1977 | Morrison, Jr. | |
| 4,074,718 A | 2/1978 | Morrison, Jr. | |
| 4,088,134 A | 5/1978 | Mazzariello | |
| 4,112,950 A * | 9/1978 | Pike | 606/42 |
| 4,127,222 A | 11/1978 | Adams | |
| 4,128,099 A | 12/1978 | Bauer | |
| 4,165,746 A | 8/1979 | Burgin | |
| 4,233,734 A | 11/1980 | Bies | |
| 4,300,564 A | 11/1981 | Furihata | |
| D263,020 S | 2/1982 | Rau, III | |
| 4,370,980 A | 2/1983 | Lottick | |
| 4,375,218 A | 3/1983 | DiGeronimo | |
| 4,416,276 A | 11/1983 | Newton et al. | |
| 4,418,692 A | 12/1983 | Guay | |
| 4,452,246 A | 6/1984 | Bader et al. | |
| 4,492,231 A | 1/1985 | Auth | |
| 4,513,271 A * | 4/1985 | Reisem | 335/205 |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,619,258 A * | 10/1986 | Pool | 606/42 |
| 4,655,215 A * | 4/1987 | Pike | 606/42 |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Xoch et al. | |
| D295,893 S | 5/1988 | Sharkany et al. | |
| D295,894 S | 5/1988 | Sharkany et al. | |
| 4,754,892 A | 7/1988 | Retief | |
| 4,763,669 A | 8/1988 | Jaeger | |
| 4,827,929 A | 5/1989 | Hodge | |
| 4,846,171 A * | 7/1989 | Kauphusman et al. | 606/15 |
| 4,887,612 A | 12/1989 | Esser et al. | |
| 4,938,761 A | 7/1990 | Ensslin | |
| 4,985,030 A | 1/1991 | Melzer et al. | |
| 5,007,908 A | 4/1991 | Rydell | |
| 5,026,370 A | 6/1991 | Lottick | |
| 5,035,695 A | 7/1991 | Weber, Jr. et al. | |
| 5,084,057 A | 1/1992 | Green et al. | |
| 5,099,840 A | 3/1992 | Goble et al. | |
| 5,116,332 A | 5/1992 | Lottick | |
| 5,147,357 A | 9/1992 | Rose et al. | |
| 5,151,102 A | 9/1992 | Xamiyama et al. | |
| 5,176,695 A | 1/1993 | Dulebohn | |
| 5,190,541 A | 3/1993 | Abele et al. | |
| 5,196,009 A | 3/1993 | Kirwan, Jr. | |
| 5,197,964 A | 3/1993 | Parins | |
| 5,215,101 A | 6/1993 | Jacobs et al. | |
| 5,217,457 A | 6/1993 | Delahuerga et al. | |
| 5,217,458 A | 6/1993 | Parins | |
| 5,217,460 A | 6/1993 | Knoepfler | |
| 5,244,462 A | 9/1993 | Delahuerga et al. | |
| 5,250,047 A | 10/1993 | Rydell | |
| 5,250,063 A | 10/1993 | Abidin et al. | |
| 5,258,001 A | 11/1993 | Corman | |
| 5,258,006 A | 11/1993 | Rydell et al. | |
| 5,261,918 A | 11/1993 | Phillips et al. | |
| 5,275,615 A | 1/1994 | Rose | |
| 5,277,201 A | 1/1994 | Stern | |
| 5,282,799 A * | 2/1994 | Rydell | 606/48 |
| 5,290,286 A | 3/1994 | Parins | |
| 5,304,203 A | 4/1994 | El-Mallawany et al. | |
| 5,308,357 A | 5/1994 | Lichtman | |
| 5,313,027 A * | 5/1994 | Inoue et al. | 200/5 A |
| 5,314,445 A | 5/1994 | Degwitz et al. | |
| 5,318,589 A | 6/1994 | Lichtman | |
| 5,324,289 A | 6/1994 | Eggers | |
| 5,326,806 A | 7/1994 | Yokoshima et al. | |
| 5,330,471 A | 7/1994 | Eggers | |
| 5,334,183 A | 8/1994 | Wuchinich | |
| 5,334,215 A | 8/1994 | Chen | |
| 5,336,220 A | 8/1994 | Ryan et al. | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,344,424 A | 9/1994 | Roberts et al. | |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |
| 5,368,600 A | 11/1994 | Failla et al. | |
| 5,376,089 A | 12/1994 | Smith | |
| 5,383,897 A | 1/1995 | Wholey | |
| 5,389,098 A | 2/1995 | Tsuruta et al. | |
| 5,389,104 A | 2/1995 | Hahnen et al. | |
| 5,391,166 A | 2/1995 | Eggers | |
| 5,391,183 A | 2/1995 | Janzen et al. | |
| 5,396,900 A | 3/1995 | Slater et al. | |
| 5,403,312 A | 4/1995 | Yates et al. | |
| 5,411,519 A | 5/1995 | Tovey et al. | |
| 5,411,520 A | 5/1995 | Nash et al. | |
| 5,413,571 A | 5/1995 | Katsaros et al. | |
| 5,415,657 A | 5/1995 | Taymor-Luria | |
| 5,422,567 A | 6/1995 | Matsunaga | |
| 5,423,810 A | 6/1995 | Goble et al. | |
| 5,425,690 A | 6/1995 | Chang | |
| 5,425,739 A | 6/1995 | Jessen | |
| 5,429,616 A | 7/1995 | Schaffer | |
| 5,431,672 A | 7/1995 | Cote et al. | |
| 5,431,674 A | 7/1995 | Basile et al. | |
| 5,437,292 A | 8/1995 | Kipshidze et al. | |
| 5,438,302 A | 8/1995 | Goble | |
| 5,441,517 A | 8/1995 | Kensey et al. | |
| 5,443,463 A | 8/1995 | Stern et al. | |
| 5,443,464 A | 8/1995 | Russell et al. | |
| 5,443,480 A | 8/1995 | Jacobs et al. | |
| 5,445,638 A | 8/1995 | Rydell et al. | |
| 5,445,658 A | 8/1995 | Durrfeld et al. | |
| 5,451,224 A | 9/1995 | Goble et al. | |
| 5,456,684 A | 10/1995 | Schmidt et al. | |
| 5,458,598 A | 10/1995 | Feinberg et al. | |
| 5,460,629 A | 10/1995 | Shlain et al. | |
| 5,462,546 A | 10/1995 | Rydell | |
| 5,472,443 A | 12/1995 | Cordis et al. | |
| 5,478,351 A | 12/1995 | Meade et al. | |
| 5,480,409 A | 1/1996 | Riza | |
| 5,484,436 A | 1/1996 | Eggers et al. | |
| 5,496,312 A | 3/1996 | Klicek | |
| 5,496,317 A | 3/1996 | Goble et al. | |
| 5,496,347 A | 3/1996 | Hashiguchi et al. | |
| 5,499,997 A | 3/1996 | Sharpe et al. | |
| 5,509,922 A | 4/1996 | Aranyi et al. | |
| 5,514,134 A | 5/1996 | Rydell et al. | |
| 5,527,313 A | 6/1996 | Scott et al. | |
| 5,531,744 A | 7/1996 | Nardella et al. | |
| 5,536,251 A | 7/1996 | Evard et al. | |
| 5,540,684 A | 7/1996 | Hassler, Jr. | |
| 5,540,685 A | 7/1996 | Parins et al. | |

| | | | | | | |
|---|---|---|---|---|---|---|
| 5,540,715 A | 7/1996 | Katsaros et al. | | 5,817,093 A | 10/1998 | Williamson, IV et al. |
| 5,542,945 A | 8/1996 | Fritzsch | | 5,820,630 A | 10/1998 | Lind |
| 5,558,671 A | 9/1996 | Yates | | 5,824,978 A * | 10/1998 | Karasik et al. ................ 200/18 |
| 5,558,672 A | 9/1996 | Edwards et al. | | 5,827,271 A | 10/1998 | Buysse et al. |
| 5,562,699 A | 10/1996 | Heimberger et al. | | 5,827,279 A | 10/1998 | Hughett et al. |
| 5,569,241 A | 10/1996 | Edwards | | 5,827,281 A | 10/1998 | Levin |
| 5,569,243 A | 10/1996 | Kortenbach et al. | | 5,827,323 A | 10/1998 | Klieman et al. |
| 5,571,100 A | 11/1996 | Goble et al. | | 5,827,548 A | 10/1998 | Lavallee et al. |
| 5,573,424 A | 11/1996 | Poppe | | 5,833,690 A | 11/1998 | Yates et al. |
| 5,573,534 A | 11/1996 | Stone | | 5,843,080 A | 12/1998 | Fleenor et al. |
| 5,573,535 A | 11/1996 | Viklund | | 5,849,022 A | 12/1998 | Sakashita et al. |
| 5,575,805 A | 11/1996 | Li | | 5,853,412 A | 12/1998 | Mayenberger |
| 5,578,052 A | 11/1996 | Koros et al. | | 5,860,976 A | 1/1999 | Billings et al. |
| 5,582,611 A | 12/1996 | Tsukagoshi et al. | | 5,876,401 A | 3/1999 | Schulze et al. |
| 5,585,896 A | 12/1996 | Yamazaki et al. | | 5,882,567 A | 3/1999 | Cavallaro et al. |
| 5,590,570 A | 1/1997 | LeMaire, III et al. | | 5,891,141 A | 4/1999 | Rydell |
| 5,603,711 A | 2/1997 | Parins et al. | | 5,891,142 A | 4/1999 | Eggers et al. |
| 5,603,723 A | 2/1997 | Aranyi et al. | | 5,893,863 A | 4/1999 | Yoon |
| 5,611,798 A | 3/1997 | Eggers | | 5,893,875 A | 4/1999 | O'Connor et al. |
| 5,620,453 A | 4/1997 | Nallakrishnan | | 5,893,877 A | 4/1999 | Gampp, Jr. et al. |
| 5,624,452 A | 4/1997 | Yates | | 5,902,301 A | 5/1999 | Olig |
| 5,626,578 A | 5/1997 | Tihon | | 5,906,630 A | 5/1999 | Anderhub et al. |
| 5,626,609 A | 5/1997 | Zvenyatsky et al. | | 5,908,420 A | 6/1999 | Parins et al. |
| 5,630,833 A | 5/1997 | Katsaros et al. | | 5,908,432 A | 6/1999 | Pan |
| 5,637,110 A | 6/1997 | Pennybacker et al. | | 5,911,719 A | 6/1999 | Eggers |
| 5,638,003 A | 6/1997 | Hall | | 5,913,874 A | 6/1999 | Berns et al. |
| 5,643,294 A | 7/1997 | Tovey et al. | | 5,921,984 A | 7/1999 | Sutcu et al. |
| 5,647,869 A | 7/1997 | Goble et al. | | 5,925,043 A | 7/1999 | Kumar et al. |
| 5,647,871 A | 7/1997 | Levine et al. | | 5,935,126 A | 8/1999 | Riza |
| 5,649,959 A | 7/1997 | Hannam et al. | | 5,938,589 A | 8/1999 | Wako et al. |
| 5,658,281 A | 8/1997 | Heard | | 5,944,718 A | 8/1999 | Dafforn et al. |
| 5,662,667 A | 9/1997 | Knodel | | 5,951,549 A | 9/1999 | Richardson et al. |
| 5,665,100 A | 9/1997 | Yoon | | 5,954,720 A | 9/1999 | Wilson et al. |
| 5,667,526 A | 9/1997 | Levin | | 5,957,923 A | 9/1999 | Hahnen et al. |
| 5,674,220 A | 10/1997 | Fox et al. | | 5,960,544 A | 10/1999 | Beyers |
| 5,681,282 A | 10/1997 | Eggers et al. | | 5,964,758 A | 10/1999 | Dresden |
| 5,688,270 A | 11/1997 | Yates et al. | | 5,976,132 A | 11/1999 | Morris |
| 5,693,051 A | 12/1997 | Schulze et al. | | 5,989,277 A | 11/1999 | LeMaire, III et al. |
| 5,695,522 A | 12/1997 | LeMaire, III et al. | | 5,997,565 A | 12/1999 | Inoue |
| 5,700,261 A | 12/1997 | Brinkerhoff | | 6,004,335 A | 12/1999 | Vaitekunas et al. |
| 5,702,390 A | 12/1997 | Austin et al. | | 6,010,516 A | 1/2000 | Hulka |
| 5,707,369 A | 1/1998 | Vaitekunas et al. | | 6,024,741 A | 2/2000 | Williamson et al. |
| 5,709,680 A | 1/1998 | Yates et al. | | 6,024,744 A | 2/2000 | Kese et al. |
| 5,716,366 A | 2/1998 | Yates | | 6,030,384 A | 2/2000 | Nezhat |
| 5,720,744 A | 2/1998 | Eggleston et al. | | 6,033,399 A | 3/2000 | Gines |
| 5,722,421 A | 3/1998 | Francese et al. | | 6,039,733 A | 3/2000 | Buysse et al. |
| 5,725,536 A | 3/1998 | Oberlin et al. | | 6,041,679 A | 3/2000 | Slater et al. |
| 5,727,428 A | 3/1998 | LeMaire, III et al. | | 6,050,996 A | 4/2000 | Schmaltz et al. |
| 5,735,848 A | 4/1998 | Yates et al. | | 6,053,914 A | 4/2000 | Eggers et al. |
| 5,743,906 A | 4/1998 | Parins et al. | | 6,053,933 A | 4/2000 | Balazs et al. |
| 5,755,717 A | 5/1998 | Yates et al. | | D424,694 S | 5/2000 | Tetzlaff et al. |
| 5,766,130 A | 6/1998 | Selmonosky | | D425,201 S | 5/2000 | Tetzlaff et al. |
| 5,766,166 A | 6/1998 | Hooven | | 6,059,782 A | 5/2000 | Novak et al. |
| 5,766,170 A | 6/1998 | Eggers | | 6,074,386 A * | 6/2000 | Goble et al. .................. 606/34 |
| 5,769,849 A | 6/1998 | Eggers | | RE36,795 E | 7/2000 | Rydell |
| 5,772,655 A | 6/1998 | Bauer et al. | | 6,083,223 A | 7/2000 | Baker |
| 5,772,670 A | 6/1998 | Brosa | | 6,086,586 A | 7/2000 | Hooven |
| 5,776,128 A | 7/1998 | Eggers | | 6,090,107 A | 7/2000 | Borgmeier et al. |
| 5,776,130 A | 7/1998 | Buysse et al. | | 6,096,037 A | 8/2000 | Mulier et al. |
| 5,779,701 A | 7/1998 | McBrayer et al. | | 6,099,550 A | 8/2000 | Yoon |
| H1745 H | 8/1998 | Paraschac | | 6,102,909 A | 8/2000 | Chen et al. |
| 5,792,137 A | 8/1998 | Carr et al. | | 6,110,171 A | 8/2000 | Rydell |
| 5,792,177 A | 8/1998 | Kaseda | | 6,113,596 A | 9/2000 | Hooven et al. |
| 5,797,927 A | 8/1998 | Yoon | | 6,113,598 A | 9/2000 | Baker |
| 5,797,938 A | 8/1998 | Paraschac et al. | | 6,117,158 A | 9/2000 | Measamer et al. |
| 5,797,941 A | 8/1998 | Schulze et al. | | 6,123,701 A | 9/2000 | Nezhat |
| 5,797,958 A | 8/1998 | Yoon | | H1904 H | 10/2000 | Yates et al. |
| 5,800,449 A | 9/1998 | Wales | | 6,126,658 A | 10/2000 | Baker |
| 5,807,393 A | 9/1998 | Williamson, IV et al. | | 6,152,923 A | 11/2000 | Ryan |
| 5,810,808 A | 9/1998 | Eggers | | 6,162,220 A | 12/2000 | Nezhat |
| 5,810,811 A | 9/1998 | Yates et al. | | 6,174,309 B1 | 1/2001 | Wrublewski et al. |
| 5,810,877 A | 9/1998 | Roth et al. | | 6,179,834 B1 | 1/2001 | Buysse et al. |
| 5,814,043 A | 9/1998 | Shapeton | | 6,179,837 B1 | 1/2001 | Hooven |

| Patent No. | Date | Inventor |
|---|---|---|
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,302,424 B1 | 10/2001 | Gisinger et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 * | 10/2002 | Cosmescu .................. 606/42 |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,616,658 B2 * | 9/2003 | Ineson ........................ 606/42 |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 * | 11/2003 | Ellman et al. ................. 606/37 |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 * | 10/2004 | Latterell et al. ............... 606/42 |
| D499,181 S | 11/2004 | Dycus et al. |
| 6,818,000 B2 | 11/2004 | Muller et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 * | 8/2005 | Mori et al. .................... 361/2 |
| 6,936,061 B2 | 8/2005 | Sasaki |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 * | 11/2005 | Goble ........................ 606/37 |
| 6,977,495 B2 * | 12/2005 | Donofrio .................... 324/127 |
| 6,979,786 B2 * | 12/2005 | Aukland et al. ........... 200/16 A |
| 6,994,707 B2 * | 2/2006 | Ellman et al. ................. 606/42 |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 * | 12/2006 | Shea et al. ..................... 361/2 |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |

| | | |
|---|---|---|
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 2002/0049442 A1 | 4/2002 | Roberts et al. |
| 2002/0107517 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0229344 A1 | 12/2003 | Dycus et al. |
| 2004/0030330 A1 | 2/2004 | Brassell et al. |
| 2004/0030332 A1 | 2/2004 | Knowlton et al. |
| 2004/0064151 A1 | 4/2004 | Mollenauer |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0162557 A1 | 8/2004 | Tetzlaff et al. |
| 2004/0176762 A1 | 9/2004 | Lawes et al. |
| 2004/0193153 A1 | 9/2004 | Sarter et al. |
| 2004/0225288 A1 | 11/2004 | Buysse et al. |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004568 A1 | 1/2005 | Lawes et al. |
| 2005/0004570 A1 | 1/2005 | Chapman et al. |
| 2005/0007766 A1* | 1/2005 | Jigamian .................. 362/157 |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0059858 A1 | 3/2005 | Frith et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0187547 A1 | 8/2005 | Sugi |
| 2005/0195550 A1* | 9/2005 | Fitzgerald et al. ........... 361/139 |
| 2005/0197659 A1 | 9/2005 | Bahney |
| 2005/0203504 A1 | 9/2005 | Wham et al. |
| 2005/0205396 A1* | 9/2005 | Aukland et al. ........... 200/16 A |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaf et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0287641 A1 | 12/2006 | Perlin |
| 2007/0016182 A1* | 1/2007 | Lipson et al. .................. 606/34 |
| 2007/0016187 A1* | 1/2007 | Weinberg et al. ............. 606/42 |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1* | 3/2007 | Isaacson et al. ................ 606/32 |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |

| | | | |
|---|---|---|---|
| 2008/0009860 A1 | 1/2008 | Odom | |
| 2008/0015575 A1 | 1/2008 | Odom et al. | |
| 2008/0021450 A1 | 1/2008 | Couture | |
| 2008/0033428 A1 | 2/2008 | Artale et al. | |
| 2008/0039835 A1 | 2/2008 | Johnson et al. | |
| 2008/0045947 A1 | 2/2008 | Johnson et al. | |
| 2008/0058802 A1 | 3/2008 | Couture et al. | |
| 2008/0082100 A1 | 4/2008 | Orton et al. | |

FOREIGN PATENT DOCUMENTS

| | | |
|---|---|---|
| DE | 2415263 | 10/1975 |
| DE | 2627679 | 1/1977 |
| DE | 4303882 | 8/1994 |
| DE | 29616210 | 1/1997 |
| DE | 19608716 | 4/1997 |
| DE | 19751106 | 5/1998 |
| DE | 19751108 | 5/1999 |
| EP | 0364216 A1 | 4/1990 |
| EP | 518230 A1 | 12/1992 |
| EP | 0 541 930 B1 | 5/1993 |
| EP | 0572131 | 12/1993 |
| EP | 584787 A1 | 3/1994 |
| EP | 0589453 A2 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 853922 A1 | 7/1998 |
| EP | 0887046 A3 | 1/1999 |
| EP | 0923907 A1 | 6/1999 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1301135 A | 4/2003 |
| EP | 1472984 A1 | 11/2004 |
| EP | 1527747 A2 | 5/2005 |
| EP | 1530952 A1 | 5/2005 |
| EP | 1535581 A2 | 6/2005 |
| EP | 1609430 A1 | 12/2005 |
| EP | 1632192 A1 | 3/2006 |
| EP | 1645238 A1 | 4/2006 |
| EP | 1645240 A2 | 4/2006 |
| EP | 1707143 A1 | 10/2006 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 * | 11/1977 |
| WO | WO89/00757 | 1/1989 |
| WO | WO 92/04873 | 4/1992 |
| WO | WO 92/06642 | 4/1992 |
| WO | WO 94/08524 A | 4/1994 |
| WO | WO94/20025 | 9/1994 |
| WO | WO 95/02369 | 1/1995 |
| WO | WO95/07662 | 3/1995 |
| WO | WO 95/07662 | 3/1995 |
| WO | WO95/15124 | 6/1995 |
| WO | WO96/05776 | 2/1996 |
| WO | WO 96/13218 | 9/1996 |
| WO | WO 97/00646 | 1/1997 |
| WO | WO 97/00647 | 1/1997 |
| WO | WO97/10764 | 3/1997 |
| WO | WO 97/24073 | 7/1997 |
| WO | WO 97/24993 | 7/1997 |
| WO | WO 98/27880 | 7/1998 |
| WO | WO 98/43264 A | 10/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/40857 | 8/1999 |
| WO | WO 99/51158 | 10/1999 |
| WO | WO 99/66850 A | 12/1999 |
| WO | WO 00/24330 | 5/2000 |
| WO | WO00/24331 | 5/2000 |
| WO | WO 00/41638 | 7/2000 |
| WO | WO00/47124 | 8/2000 |
| WO | WO 00/53112 | 9/2000 |
| WO | WO 01/17448 A | 3/2001 |
| WO | WO 01/54604 | 8/2001 |
| WO | WO02/07627 | 1/2002 |
| WO | WO 02/07627 | 1/2002 |
| WO | WO 02/067798 A1 | 9/2002 |
| WO | WO 02/080783 | 10/2002 |
| WO | WO02/080783 | 10/2002 |
| WO | WO02/080784 | 10/2002 |
| WO | WO 02/080784 | 10/2002 |
| WO | WO02/080785 | 10/2002 |
| WO | WO 02/080785 | 10/2002 |
| WO | WO02/080786 | 10/2002 |
| WO | WO 02/080786 | 10/2002 |
| WO | WO 02/080793 | 10/2002 |
| WO | WO02/080793 | 10/2002 |
| WO | WO 02/080794 | 10/2002 |
| WO | WO02/080794 | 10/2002 |
| WO | WO 02/080795 | 10/2002 |
| WO | WO 02/080796 | 10/2002 |
| WO | WO 02/080797 | 10/2002 |
| WO | WO02/080797 | 10/2002 |
| WO | WO 02/080798 | 10/2002 |
| WO | WO 02/080799 | 10/2002 |
| WO | WO02/081170 | 10/2002 |
| WO | WO 02/081170 | 10/2002 |
| WO | WO 03/090630 A3 | 11/2003 |
| WO | WO 2004/032776 A1 | 4/2004 |
| WO | WO 2004/032777 | 4/2004 |
| WO | WO2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO2005/004735 | 1/2005 |

WO    WO 2005/110264    11/2005

OTHER PUBLICATIONS

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, Nc; Date: Aug. 2003.*
"Reducing Needlestick Injuries in the Operating Room" Sales/Product Literature 2001.*
W. Scott Helton, "LigeSure Vessel Sealing System: Revolutionary Hemostasis Product for General Surgery"; Sales/Product Literature 1999.*
McLellan et al. "Vessel Sealing for Hemostasis During Gynecologic Surgery" Sales/Product Literature 1999.*
E. David Crawford "Use of a Novel Vessel Sealing Technology in Management of the Dorsal Veinous Complex" Sales/Product Literature 2000.*
Jarrett et al., "Use of the LigeSure Vessel Sealing System for Peri-Hilar Vessels in Laparoscopic Nephrectomy" Sales/Product Literature 2000.*
E. David Crawford "Evaluation of a New Vessel Sealing Device in Urologic Cancer Surgery" Sales/Product Literature 2000.*
Int'l Search Report EP 98944778.4 dated Oct. 31, 2000.*
Int'l Search Report EP 98958575.7 dated Sep. 20, 2002.*
Int'l Search Report EP 04013772.1 dated Apr. 1, 2005.*
Int'l Search Report EP 04027314.6 dated Mar. 10, 2005.*
Int'l Search Report EP 04027479.7 dated Mar. 8, 2005.*
Int'l Search Report EP 04027705.5 dated Feb. 3, 2005.*
Int'l Search Report PCT/US98/18640 dated Jan. 29, 1999.*
Int'l Search Report PCT/US98/23950 dated Jan. 14, 1999.*
Int'l Search Report PCT/US99/24869 dated Feb. 3, 2000.*
Int'l Search Report PCT/US01/11218 dated Aug. 14, 2001.*
Int'l Search Report PCT/US01/11340 dated Aug. 16, 2001.*
Int'l Search Report PCT/US01/11420 dated Oct. 16, 2001.*
Int'l Search Report PCT/US02/01890 dated Jul. 25, 2002.*
Int'l Search Report PCT/US02/11100 dated Jul. 16, 2002.*
Int'l Search Report PCT/US04/03436 dated Mar. 3, 2005.*
Int'l Search Report PCT/US04/13273 dated Dec. 15, 2004.*
Int'l Search Report PCT/USO4/15311 dated Jan. 12, 2005.*
Int'l Search Report EP06014461.5, Oct. 20, 2006.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford at al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Crawford et al. "Use of the LigaSure Vessel Seating System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With the LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.

Johnson et al. "Evaluation of a Bipolar electrothermal Vessel Sealing Device in Hemorrhoidectomy" Sales/Product Literature; Jan. 2004.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.

* cited by examiner

SWITCH MECHANISMS FOR SAFE ACTIVATION OF ENERGY ON AN ELECTROSURGICAL INSTRUMENT

BACKGROUND

1. Technical Field

The present disclosure relates to switch mechanisms for safe activation of energy on an electrosurgical instrument. More particularly, the present disclosure relates to switching mechanisms for engaging high energy contacts prior to activation of the energy source.

2. Background of Related Art

Many surgical procedures are enhanced by the use of energy during the procedure. Special surgical instruments have been developed to utilize the energy during the surgical procedures. These instruments are typically termed "electrosurgical instruments" and include provisions for utilizing energy to cauterize, cut, etc. tissue during various surgical procedures. Typically, during these surgical procedures, a distal portion of the electrosurgical instrument is engaged with tissue and the energy source turned on, or activated, by a switching mechanism to supply the energy to tissue. The energy applied to the tissue may take various forms including energy sources ranging from a microwave to direct current, radiofrequency, etc.

Issues may arise within the switch mechanism itself during activation of the electrosurgical instrument. These electrical surgical instruments include switching mechanisms which utilize materials such as copper, brass, gold, silver, plastics, etc. for the high-energy contacts and which are highly efficient in transmitting energy. However, due to the nature of these materials, they are susceptible to damage as the contacts are brought together while energized. Specifically, "arcing", or jumping of the energy across the contacts prior to the contacts being brought together, may result as the high-energy contacts are brought together with the high-energy source switched on. This arcing often results in damage to the high-energy contacts themselves reducing the efficiency of the contacts. Furthermore, during most surgical procedures utilizing electrosurgical instruments, multiple activations of the surgical instrument are usually required. This results in multiple instances of arcing across the high-energy contacts such that each arcing event results in a progressive degradation of the quality and efficiency of the high-energy contacts. Thus, as the electrosurgical instrument is used multiple times during the surgery it becomes progressively less efficient.

Thus, it is desirable to provide a safe switching mechanism which is capable of connecting the high-energy contacts prior to activating the high-energy source in order to avoid problems such as arcing and the resultant damage to the high-energy contacts.

SUMMARY

There is disclosed a safe activation switching mechanism having a pair of high energy contacts including a first high-energy contact and a second high-energy contact and a pair of activation contacts including a first activation contact and a second activation contact. The switching mechanism also includes an actuator having a first portion for engaging the first high-energy contact with the second high-energy contact and a second portion for engaging the first activation contact with the second activation contact.

In one embodiment, the actuator includes a driver having a first connector for engagement with the pair of high-energy contacts and a second connector for engagement with the pair of activation contacts. The actuator includes a biasing member positioned between the first and second connectors. The actuator can be vertically or horizontally movable.

In another embodiment, the actuator includes a first wiper and a second wiper, the first and second wiper are spaced apart such that the first wiper contacts the first high-energy contact in advance of the second wiper contacting the first activation contact. The second high-energy contact and the second activation contact are a common contact.

In one embodiment, the actuator includes a driver having a first elongated drive surface for engagement with the first high-energy contact and a second elongated drive surface for engagement with the second high-energy contact. The first elongated drive surface is substantially longer than the second elongated drive surface to insure that contact with the first connector remains in contact before the second switch is activated.

In one embodiment, the pair of high-energy contacts includes a dome switch and the pair of activation contacts includes a dome switch.

In another embodiment, an actuator includes a first magnet for engaging the pair of high-energy contacts and a second magnet for engaging the pair of activation contacts. The first and second magnets are connected together. The first high-energy contact includes a first flexible arm and the first activation contact includes a second flexible arm, the first and second flexible arms are engageable with a common contact.

There is also provided an electrosurgical instrument assembly including an energy generator and an electrosurgical instrument connected to the energy generator, the electrosurgical instrument includes a switch mechanism having a pair of high-energy contacts, a pair of activation contacts, and an actuator having a first portion for engaging the high-energy contacts in advance of engaging the activation contacts.

There is also provided a method of safely activating a high energy electrosurgical instrument by providing a switch mechanism including a pair of high energy contacts, a pair of activation contacts and actuator engageable with the high-energy contacts and the activation contacts. The actuator is moved into engagement with the pair of high-energy contacts and subsequently the actuator is moved into engagement with the pair of activation contacts.

DESCRIPTION OF THE DRAWINGS

Various embodiments of the presently disclosed switching mechanisms are disclosed herein with reference to the drawings, wherein.

DETAILED DESCRIPTION

Embodiments of the presently disclosed switching mechanisms will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
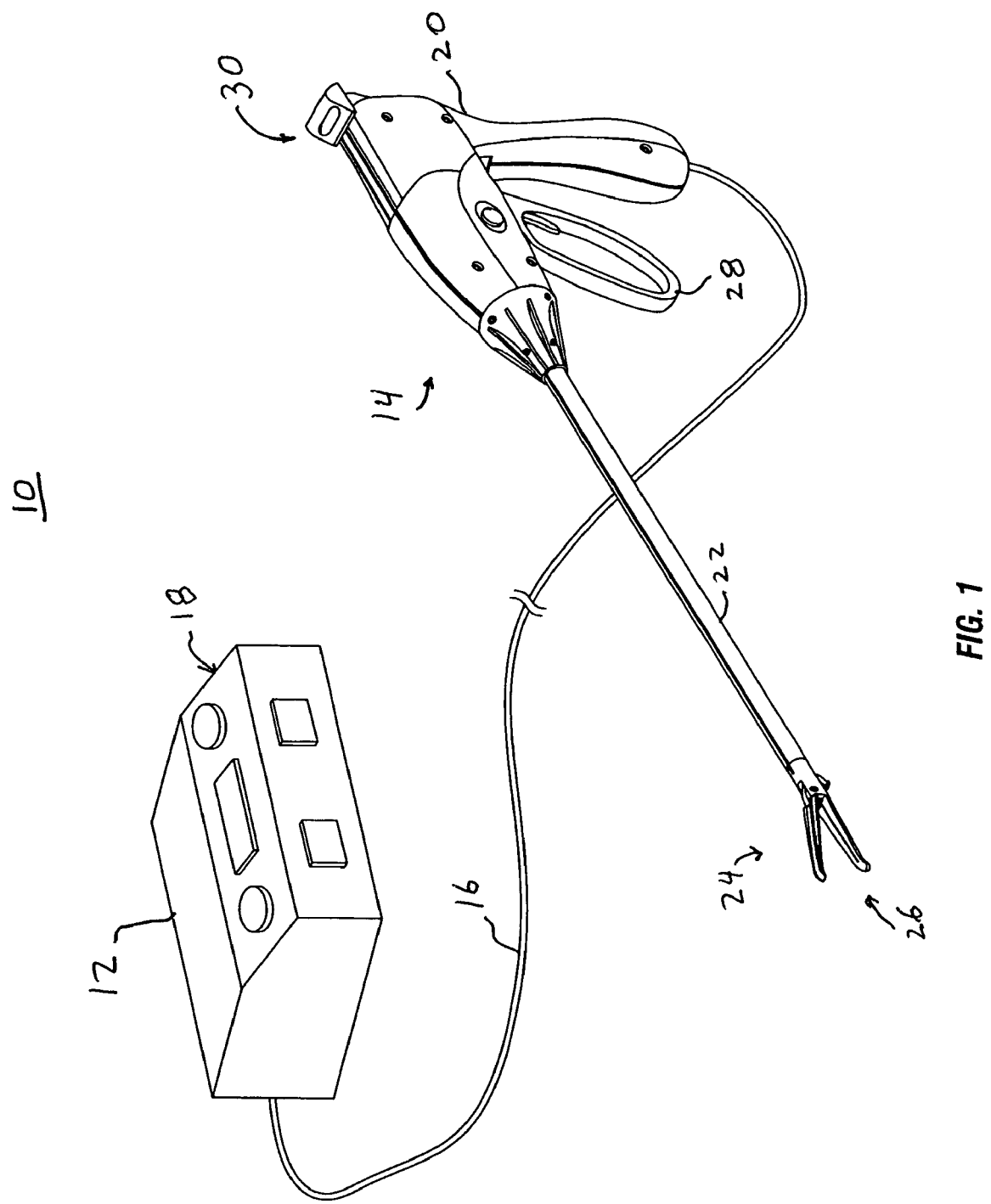
FIG. 1 is a perspective view of an electrosurgical instrument and energy generator for use with the disclosed switching mechanisms.

Referring to FIG. 1, there is disclosed an embodiment of an electrosurgical instrument assembly 10 of the type used during certain surgical procedures. Electrosurgical instrument assembly 10 generally includes an energy generator 12 and an electrosurgical instrument 14 connected by a transmission cable 16. Energy generator 12 may supply various sources of "high" energy to the electrosurgical instrument 14. As used herein, the term "high-energy" refers to various sources of energy, i.e. high current/high voltage, applied to tissue during the electrosurgical procedures. These types of high energy may include, energy sources ranging from microwave to direct current, radiofrequency, etc.

Electrosurgical instrument 14 generally includes a handle 20 having an elongate tubular member 22 extending distally therefrom. An end effector 24, such as, for example, a pair of jaws 26, is provided at a distal end of elongate tubular member 22 for engaging and operating on tissue. A pivoting handle, or trigger 28, is provided on handle 20 to operate end effector 24. A safe switch mechanism 30 is provided on handle 20 to activate energy generator 12 and provide a high-energy source to end effector 24.

During a surgical procedure requiring the application of high-energy to tissue, electrosurgical instrument 14 is manipulated such that end effector 24 is positioned about tissue. Trigger 28 is operated to cause end effector 24 to perform its intended function on the tissue, such as, for example, grasping, stapling, cutting etc. Thereafter, switch mechanism 30 can be activated to supply high-energy to the tissue. Switch mechanism 30 operates in a manner described hereinbelow with regard to the various disclosed embodiments such that the high-energy contacts contained there in are not damaged or degraded allowing electrosurgical instrument 14 to be repeatedly used with the same degree of efficiency. Specifically, switch mechanism 30 contains a multi-pole contact switch having a low-level activation line, or contacts, which is contacted or connected after the contact or connection for the high-energy source is made, to activate the energy source. The reverse order of operation will deactivate the high-energy source before the high-energy contacts are separated. By operating the high-energy contacts and low-level activation line or contacts in this order, arcing associated with direct switching of the high-energy source and the negative effects associated therewith are avoided.

While switch mechanism 30 is disclosed as being incorporated into electrosurgical instrument 14, switch mechanism 30 may be provided on either energy generator 12 or electrosurgical instrument 14. When switch mechanism 30 is provided on electrosurgical instrument 14, the various components of electrosurgical instrument 14 are constructed such that the high-energy source is insulated from the patient in various ways as is known in the art.

Figure 2:
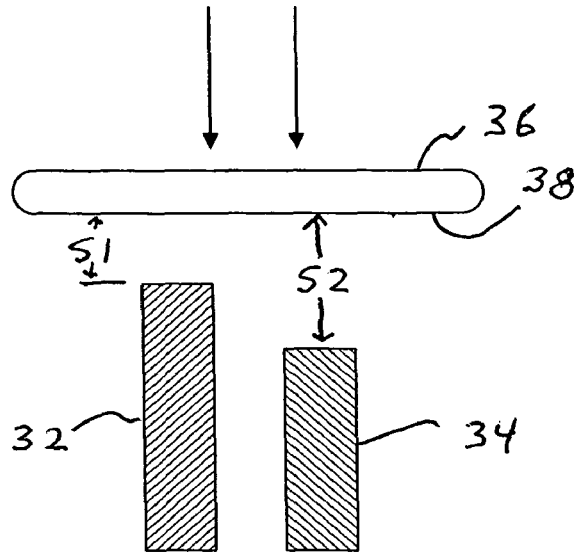
FIG. 2 is a schematic view of a first embodiment of a vertically actuated switching mechanism.

Referring now to FIG. 2, the general components and operation of switch mechanism 30 will now be described. Switch mechanism 30 generally includes a pair of high-energy contacts 32 and a pair of activation contacts 34. High-energy contacts 32 provide a source of high energy to electrosurgical instrument 14 from generator 12 while activation contacts 34 activate and deactivate the high-energy source. An actuator 36, having a driving surface 38, is provided to connect the poles of high-energy contacts 32 and activation contacts 34.

In use, actuator 36 is depressed vertically through an initial stroke S1 to engage driving surface 38 with the high-energy contacts 32 thereby connecting the poles contained within high-energy contacts 32. This allows high-energy contacts 32 to be connected prior to the activation of the energy source supplied by energy generator 12 thereby completely eliminating any chance of arcing across high-energy contacts 32. Thereafter, actuator 36 is moved through a second stroke S2, which is greater than stroke S1, to engage and connect activation contacts 34. This activates energy generator 12 thereby supplying a source of high energy through high-energy contacts 32 to electrosurgical instrument 14. While not specifically shown, as actuator 36 is moved through the second stroke S2, high-energy contacts 32 are depressed along with actuator 36.

Once electrosurgical instrument 14 has been used to operate on tissue, switch mechanism 30 can be turned off. Specifically, as actuator 36 is released, it returns vertically through stroke S2 thereby disengaging activation contacts 34 while maintaining the connection between high-energy contacts 32. This prevents destructive arcing between high-energy contacts 32 as energy generator 12 is turned off. Further release of actuator 36 through stroke S1 disengages high-energy contacts 32.

Figure 3:
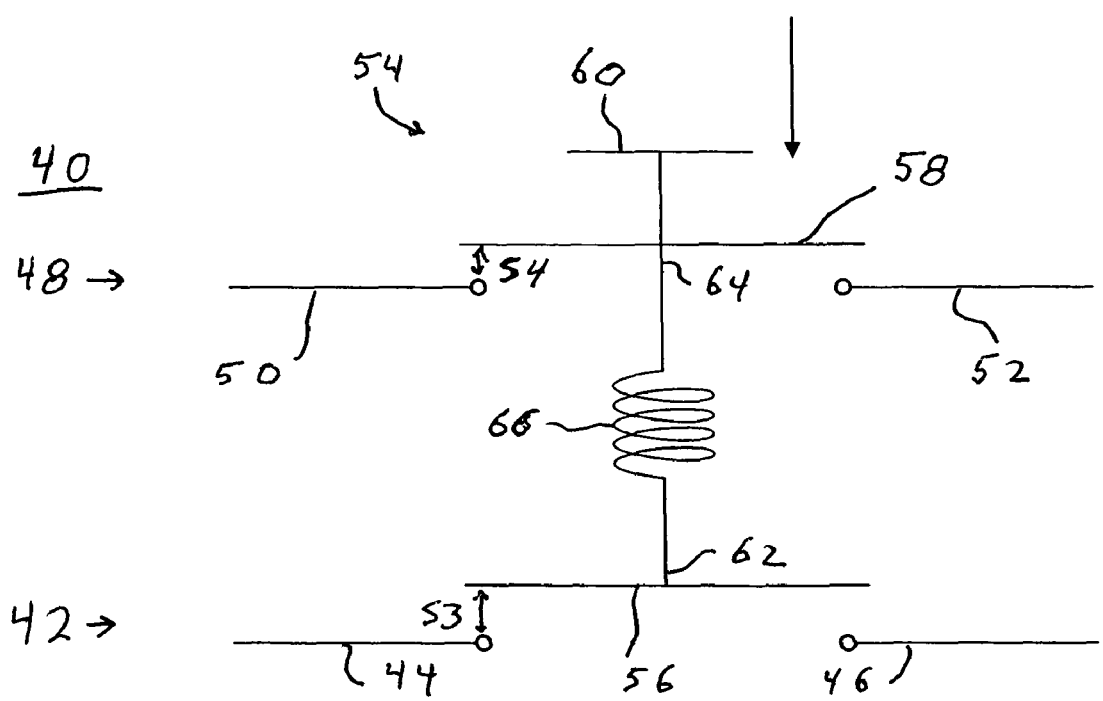
FIG. 3 is a schematic view of a second embodiment of a vertically actuated switching mechanism.

Referring now to FIG. 3, an alternative embodiment of a vertically actuated safe switch mechanism is disclosed. Switch mechanism 40 generally includes a pair of high-energy contacts 42, including a first pole or high-energy contact 44 and a second pole or high-energy contact 46, and a pair of low-level activation contacts 48, including a first activation contact 50 and a second activation contact 52. An actuator 54 is provided to initially bring first and second high-energy contacts 44 and 46 together and subsequently connect first activation contact 50 with second activation contact 52 to activate energy generator 12. Actuator 54 includes a first connector 56 to connect first high-energy contact 44 with second high-energy contact 46. Actuator 54 also includes a second connector 58 to connect first activation contact 50 with second activation contact 52. Actuator 54 is provided with a driver 60 to move first and second connectors 56 and 58. Driver 60 is connected to first connector 56 at a first point 62 and connected to second connector 58 and a second point 64.

A biasing member 66 is provided intermediate first connector 56 and second connector 58. Biasing member 66 can be formed of any resilient material such as a spring or an elastomer. Biasing member 66 is provided to maintain first connector 56 in engagement with pair of high-energy contacts 42 as second connector 58 is brought into engagement with pair of activation contacts 48 to prevent arcing as switch mechanism 40 is turned on. Additionally, biasing member 66 maintains first connector 56 in engagement with pair of high-energy contacts 42 as second connector 58 is released from activation contacts 48 thereby eliminating arcing as switch mechanism 40 is turned off.

In use, a surgical procedure is performed with electrosurgical instrument 14 in a manner described hereinabove. Switch mechanism 40 is actuated to provide a high-energy source to end effector 24. Specifically, driver 60 is depressed to move first connector 56 through a stroke S3 thereby connecting first high-energy contact 44 with second high-energy contact 46 prior to activation of an energy source thereby preventing any arcing while activating switch mechanism 40. Further depression of driver 60 moves second connector 58 against the bias of biasing member 66 and through a further stroke S4 to connect first activation contact 50 with second activation contact 52 to turn on energy generator 12 and provided a source of high-energy to electrosurgical instrument 14. Upon release of driver 60, second connector 58 is brought out of engagement with first and second activation contacts 50 and 52 while biasing member 66 maintains first connector 56 in engagement with first and second high-energy contacts 44 and 46. This prevents arcing while turning off switch mechanism 40.

Figure 4:
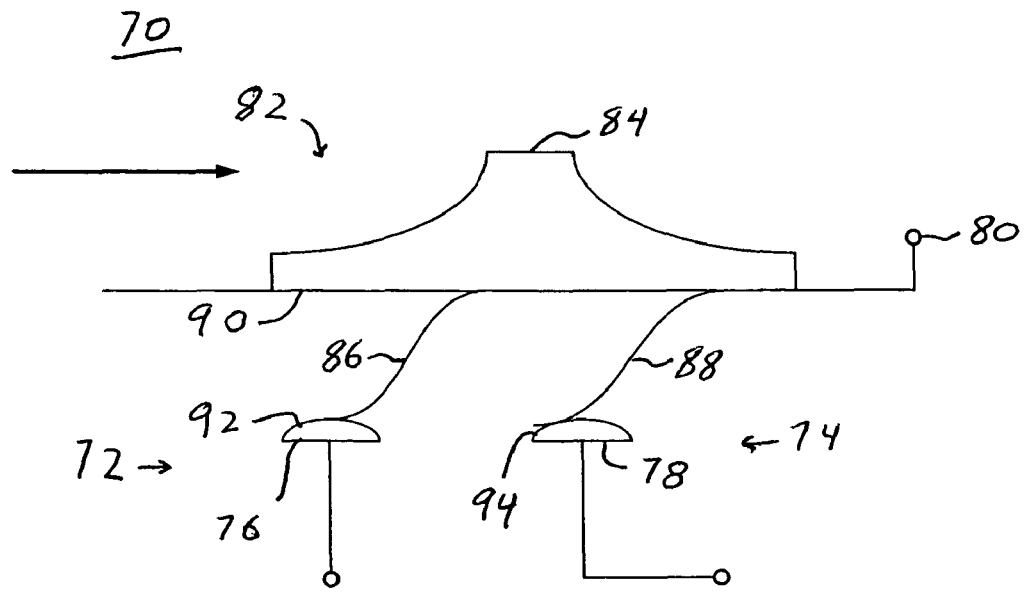
FIG. 4 is a schematic view of a first embodiment of a horizontally actuated switching mechanism.

Further safe switching mechanisms, which are horizontally actuated, will now be described with reference to FIGS. 4-7. Referring to FIG. 4, a horizontally actuated switch mechanism 70 is disclosed which includes a pair of high-energy contacts 72 and a pair of activation contacts 74. Pair of high-energy contacts 72 includes a first high-energy contact 76 and pair of activation contacts 74 includes a first activation contact 78. Pair of high-energy contacts 72 and pair of activation contacts 74 share a common second contact 80. Switch mechanism 70 also includes a horizontally movable actuator 82 to initially connect first high-energy contact 76 with common contact 80 and subsequently connect first activation contact 78 with common contact 80. Actuator 82 further includes a first connector or wiper 86 and a second connector or wiper 88. Wiper 86 is provided to connect first high-energy contact 76 with common contact 80 and wiper 88 is provided to connect first activation contact 78 with common contact 80.

Wiper 86 extends from a bottom surface 90 of driver 84 and contacts a first surface 92 on first high-energy contact 76. Similarly, wiper 88 extends from bottom surface 90 of driver 84 and contacts a surface 94 of first activation contact 78. Wipers 86 and 88 are spaced along bottom surface 90 of driver 84 such that horizontal movement of driver 84 results in wiper 86 initially contacting first high-energy contact 76 in advance of wiper 88 contacting first activation contact 78. Thus, in use, as driver 84 is moved horizontally through a first stroke, wiper 86 engages first high-energy contact 76 to thereby connect first high-energy contact 76 with common contact 80. This completes the connection between high-energy contacts 76 and 80 prior to activation energy generator 12 thereby preventing any chance of arcing between high-energy contacts 76 and 80. As driver 84 is moved horizontally through a second stroke, wiper 86 continues to ride on first high-energy contact surface 92 as wiper 88 is brought into engagement with first activation surface 94 of first activation contact 78. Engagement of wiper 88 with first activation contact 78 completes the connection between first activation contact 78 and common contact 80 to activate energy generator 12.

Once the electrosurgical procedure has been completed, movement of driver 84 in the opposite direction brings wiper 88 out of engagement with first activation contact 78 to deactivate energy generator 12 while maintaining the connection between first high-energy contact 76 and common contact 80 thereby reducing any chance of arcing as energy generator 12 is deactivated. Finally, further movement of driver 84 moves wiper 86 out of engagement with first high-energy contact 76.

Figure 5:
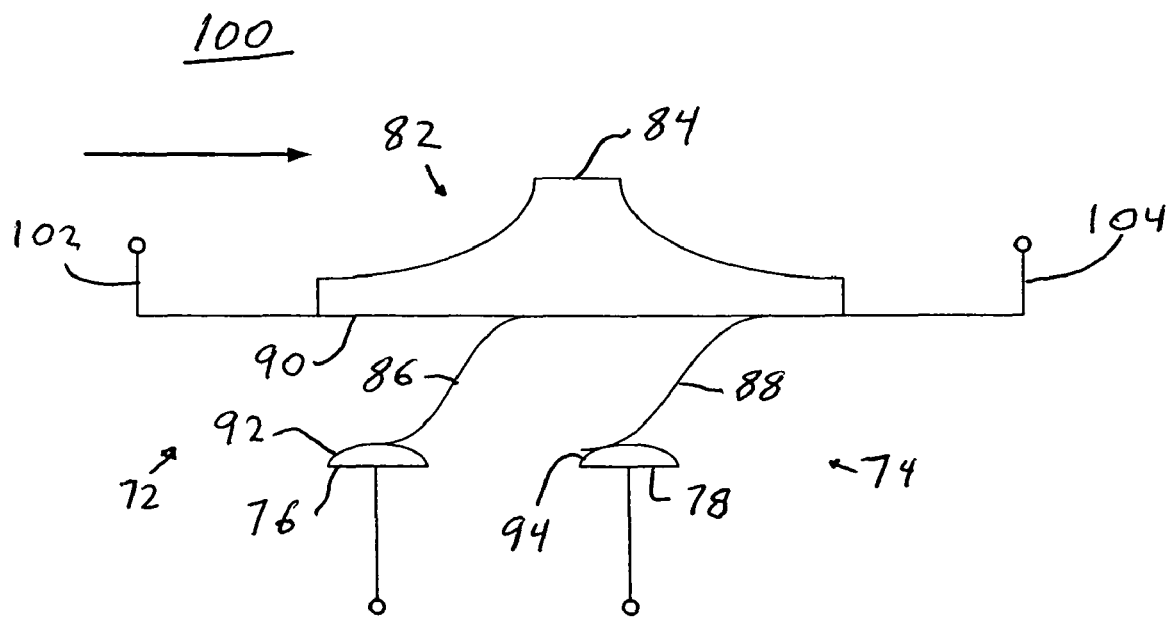
FIG. 5 is a schematic view of a second embodiment of a horizontally actuated switching mechanism.

Referring now to FIG. 5, there is disclosed a further embodiment of a switch mechanism 100 which is substantially identical to switch mechanism 70. However, switch mechanism 100 incorporates a separate second high-energy contact 102 and a separate second activation contact 104 in place of common contact 80 disclosed in switch mechanism 70. Thus, in use, initial movement of driver 84 through a first stroke brings wiper 86 into engagement with first high-energy contact surface 92 of first high-energy contact 76 to connect first high-energy contact 76 with second high-energy contact 102. Further horizontal movement of driver 84 through a second stroke brings wiper 88 into engagement with first activation surface 94 of first activation contact 78 to connect first activation contact 78 with second activation contact 104.

Reverse movement of driver 72 operates in a similar manner to initially disengage first and second activation contacts 78 and 104 to turn off the energy supplied by energy generator 12 and subsequently disengage first and second high-energy contacts 76 and 102, respectively. As with prior embodiments, engagement of the high energy contacts prior to engagement of the activation contacts avoids arcing during activation of energy generator 12 and, similarly, disengagement of the activation contacts prior to disengagement of the high-energy contacts avoids arcing during deactivating energy generator 12.

Figure 6:
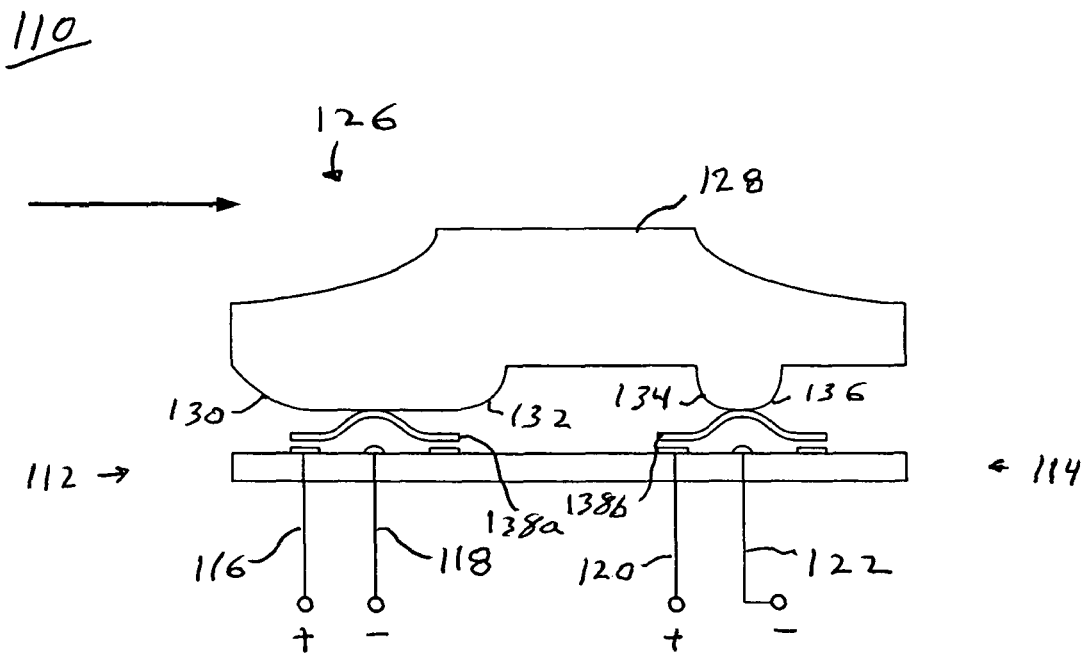
FIG. 6 is a schematic view of a third embodiment of a horizontally actuated switching mechanism.

A further embodiment of a horizontally-actuated safe switch mechanism is disclosed with reference to FIG. 6. Switch mechanism 110 is manufactured utilizing dome switches capable of handling 1.5 A, 300V and 10V, 500 ma, and from materials capable of withstanding the surgical environment defined in IEC 60601-2-2. Switch mechanism 110 includes a pair of high-energy contacts 112 and a pair of activation contacts 114. Pair of high-energy contacts 112 includes a first high-energy contact 116 and a second high-energy contact 118. Pair of activation contacts 114 includes a first activation contact 120 and a second activation contact 124. An actuator 126, including a driver 128, is provided to engage the various contacts. Specifically, driver 128 includes a first elongated drive surface 130 having a leading edge 132. Driver 128 also includes a second elongated drive surface 134 having a leading edge 136. First elongated drive surface 130 is substantially longer than second elongated drive surface 134 in order to engage first high-energy contact 116 with second high-energy contact 118 prior to engagement of pair of activation contacts 114.

As noted hereinabove, switch mechanism 110 is provided with a pair of typical dome switches 138a and 138b, which function in known manner, to engage pair of high-energy contacts 112 and pair of activation contacts 114 in response to horizontal motion of driver 128.

In use, as with prior embodiments, subsequent to or in connection with the performance of the surgical procedure with electrosurgical instrument 14, switch mechanism 110 is activated by moving driver 128 horizontally. As driver 128 is moved horizontally through a first stroke, leading edge 132 of elongated drive surface 130 engages dome switch 138a to initially bring first high-energy contact 116 into engagement with second high-energy contact 118. Further horizontal movement of driver 128 through a second stroke causes leading edge 136 of second elongated drive surface 134 to engage second dome switch 138b thereby bringing first activation contact 120 into engagement with second activation contact 124 to activate energy generator 12 and provide a source of energy to electrosurgical instrument 14. As with prior embodiments, switch mechanism 110 allows high-energy contacts 116 and 118 to be connected prior to activating energy generator 12 thereby avoiding any arcing, and resulting damage, as high-energy contacts 116 and 118 are brought together. Similarly, as driver 128 is moved horizontally in the reverse direction, dome switch 138b disengages first activation contact 120 from second activation contact 124 prior to disconnecting first pair of high-energy contacts 112 to prevent arcing while deactivating energy generator 12.

Figure 7:
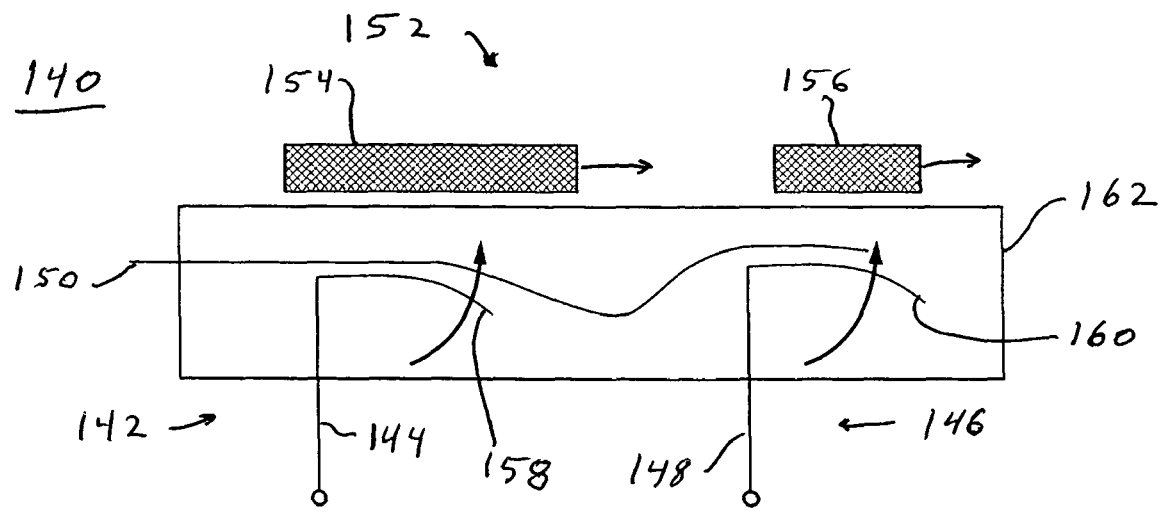
FIG. 7 is a schematic view of a fourth embodiment of a horizontally actuated switching mechanism.

Referring to FIG. 7, there is disclosed a further horizontally-actuated safe switching mechanism 140 which utilizes magnets in order to bring the various contacts together. Switch mechanism 140 includes a pair of high-energy contacts 142, including a first high-energy contact 144, and a pair of activation contacts 146 including a first activation contact 148. Similar to switch mechanism 70 described hereinabove, switch mechanism 140 is provided with a common contact 150 which serves as second contacts for pair of high-energy contacts 142 and pair of activation contacts 146.

Switch mechanism 140 includes an actuator 152 including a first magnet 154 and a second magnet 156. First and second magnets 154, 156 may be interconnected to move horizontally simultaneously (or may be provided separately to be individually actuated). In order to connect first high-energy contact 144 with common contact 150, first high-energy contact 144 includes a high-energy arm 158. High energy arm 158 is sufficiently flexible to be drawn into engagement with common contact 150 in response to movement of magnet 154. Similarly, first activation contact 148 includes an activation arm 160. Activation arm 160 is sufficiently flexible to be drawn into engagement with common contact 150 in response to movement of magnet 156. Common contact 150 may be secured within a housing 162 in order to avoid any movement of common contact 150 in response to motion of magnets 154 or 156.

In use, magnets 154 and 156 are moved horizontally through an initial stroke. Magnet 154 is sufficiently longer than magnet 156 such that magnet 154 draws high-energy contact arm 158 into engagement with common contact 150 in advance of engagement of pair of activation contacts 146. Thus, engagement of pair of high-energy contacts 142 is accomplished prior to engagement of pair of activation contacts 146 to prevent arcing between high-energy contacts 142 as energy generator 12 is activated. Magnets 154 and 156 are then moved through a second stroke to draw magnet 156 over activation contact arm 160 thereby bringing activation contact arm 160 into engagement with common contact 150 to activate energy generator 12 and provide a source of high-energy to electrosurgical instrument 14. As with previous embodiments, once the electrosurgical procedure has been completed, movement of actuator 152 in the reverse horizontal direction initially draws magnets 154 and 156 such that magnet 156 releases activation arm 160 from common contact 150 to deactivate energy generator 12 thus preventing arcing between pair of high-energy contacts 142. Thereafter, further movement of actuator 152 in the reverse horizontal direction moves magnet 154 such that magnet 154 releases high energy contact arm 158 from common contact 150.

It will be understood that various modifications may be made to the embodiments disclosed herein. For example, while the disclosed embodiments of the safe switch mechanism have been described as being vertically or horizontally actuated, the relative motions are interchangeable or combinable depending upon the orientation of the switch within the energy generator or electrosurgical instrument. Further, the motion of the actuator within the switch mechanism need not be linear but may also include rotary functions to initially engage high-energy contacts in advance of activation of an energy generator. Additionally, the disclosed switching mechanisms need not be incorporated directly into either the energy generator or the electrosurgical instrument but may be provided intermediate or externally thereto in a form, such as, for example, a foot pedal and switch, etc. Therefore, the above description should not be construed as limiting, but merely as exemplifications of particular embodiments. Those skilled in the art will envision other modifications within the scope and spirit of the claims appended hereto.

The invention claimed is:

1. A safe activation switching mechanism coupling an electrosurgical instrument and an electrosurgical generator comprising:

a pair of high-energy contacts including a first high-energy contact and a second high-energy contact interconnecting an electrosurgical instrument and an electrosurgical generator;

a pair of low-energy activation contacts including a first low-energy activation contact and a second low-energy activation contact coupled to the electrosurgical generator and configured to activate the electrosurgical generator; and an actuator having a first portion configured to engage the first high-energy contact and the second high-energy contact and a second portion configured to engage the first low-energy activation contact and the second low-energy activation contact; wherein initially engaging the first and second high-energy contacts operably connects the electrosurgical instrument to the energy source and subsequently the first and second low-energy activation contacts activate the electrosurgical generator to supply electrosurgical energy solely through the pair of high-energy contacts to eliminate arcing between the high-energy contacts.

2. The switching mechanism as recited in claim 1, wherein the actuator includes a driver having a first connector for engagement with the pair of high-energy contacts and a second connector for engagement with the pair of low-energy activation contacts.

3. The switching mechanism as recited in claim 2, wherein the actuator includes a biasing member positioned between the first and second connectors.

4. The switching mechanism as recited in claim 1, wherein the actuator is vertically movable.

5. The switching mechanism as recited in claim 1, wherein the actuator is horizontally movable.

6. The switching mechanism as recited in claim 1, wherein the actuator includes a first wiper and a second wiper, the first and second wipers are spaced apart such that the first wiper contacts and remains in contact with the first high-energy contact in advance of the second wiper contacting the first low-energy activation contact.

7. The switching mechanism as recited in claim 1, wherein the second high-energy contact and the second low-energy activation contact are a common contact.

8. The switching mechanism as recited in claim 1, wherein the actuator includes a driver having a first elongated drive surface for engagement with the first high-energy contact and the second high-energy contact.

9. The switching mechanism as recited in claim 8, wherein the driver includes a second elongated drive surface for engagement with the first low-energy activation contact and the second low-energy contact.

10. The switching mechanism as recited in claim 9, wherein the first elongated drive surface is substantially longer than the second elongated drive surface.

11. The switching mechanism as recited in claim 1, wherein the pair of high-energy contacts includes a dome switch.

12. The switching mechanism as recited in claim 1, wherein the pair of low-energy activation contacts includes a dome switch.

13. The switching mechanism as recited in claim 8, wherein the driver is horizontally movable.

14. The switching mechanism as recited in claim 1, wherein the actuator includes a first magnet for engaging the pair of high-energy contacts and a second magnet for engaging the pair of low-energy activation contacts.

15. The switching mechanism as recited in claim 14, wherein the first and second magnets are connected together.

16. The switching mechanism as recited in claim 14, wherein the second high-energy contact and the second low-energy activation contact are a common contact.

17. The switching mechanism as recited in claim 16, wherein the first high-energy contact includes a first flexible arm and the first low-energy activation contact includes a second flexible arm, the first and second flexible arms engageable with the common contact.

18. The switching mechanism as recited in claim 1 wherein the actuator is moveable in both a horizontal and a vertical direction to engage at least one of the first and second high energy contacts and the first and second low-energy activation contacts.

19. An electrosurgical instrument assembly comprising:
an electrosurgical generator; and
an electrosurgical instrument connected to the electrosurgical generator, the electrosurgical instrument including:
  a switch mechanism having a pair of high-energy contacts interconnecting the electrosurgical instrument and the electrosurgical generator;
  a pair of low-energy activation contacts coupled to the electrosurgical generator and adapted to activate the electrosurgical generator; and
  an actuator having a first portion for engaging the high-energy contacts in advance of engaging the low-energy activation contacts to supply electrosurgical energy solely through the pair of high-energy contacts to eliminate arcing between the high-energy contacts.

20. A method of safely activating a high electrosurgical instrument comprising the steps of:
providing a switch mechanism including a pair of high-energy contacts interconnecting the electrosurgical instrument and an electrosurgical generator a pair of low-energy activation contacts coupled to the electrosurgical generator and an actuator engageable with the high-energy contacts and the low-energy activation contacts;
moving the actuator into engagement with the pair of high-energy contacts to interconnect the electrosurgical instrument and an electrosurgical generator; and
subsequently moving the actuator into engagement with the pair of low-energy activation contacts to activate the electrosurgical generator to supply electrosurgical energy solely through the pair of high-energy contacts to eliminate arcing between the high-energy contacts.

* * * * *